United States Patent
Fujita

(10) Patent No.: US 12,337,580 B2
(45) Date of Patent: Jun. 24, 2025

(54) APPARATUS AND METHOD FOR MANUFACTURING LAMINATE

(71) Applicant: ZUIKO CORPORATION, Osaka (JP)

(72) Inventor: Hideki Fujita, Osaka (JP)

(73) Assignee: ZUIKO CORPORATION, Osaka (JP)

( * ) Notice: Subject to any disclaimer, the term of this patent is extended or adjusted under 35 U.S.C. 154(b) by 126 days.

(21) Appl. No.: 18/036,174

(22) PCT Filed: Oct. 19, 2021

(86) PCT No.: PCT/JP2021/038548
§ 371 (c)(1),
(2) Date: May 10, 2023

(87) PCT Pub. No.: WO2022/107531
PCT Pub. Date: May 27, 2022

(65) Prior Publication Data
US 2023/0398774 A1    Dec. 14, 2023

(30) Foreign Application Priority Data
Nov. 17, 2020   (JP) .................................. 2020-191075

(51) Int. Cl.
   *B32B 37/18*     (2006.01)
   *A61F 13/15*     (2006.01)
   (Continued)

(52) U.S. Cl.
   CPC ........ *B32B 37/18* (2013.01); *A61F 13/15764* (2013.01); *B32B 5/022* (2013.01);
   (Continued)

(58) Field of Classification Search
   CPC ......... B32B 37/18; B32B 5/022; B32B 5/265; B32B 37/0046; B32B 37/10; B32B 38/18;
   (Continued)

(56) References Cited

U.S. PATENT DOCUMENTS

2003/0001042 A1   1/2003   Betti et al.
2004/0123954 A1*  7/2004   Yoneoka ........... A61F 13/15593
                                                         156/229
(Continued)

FOREIGN PATENT DOCUMENTS

JP   H08-120433 A   5/1996
JP   2003-38565 A   2/2003
(Continued)

OTHER PUBLICATIONS

International Search Report for corresponding Application No. PCT/JP2021/038548, mailed Dec. 28, 2021.

*Primary Examiner* — Cynthia L Schaller
(74) *Attorney, Agent, or Firm* — Renner, Otto, Boisselle & Sklar, LLP

(57) ABSTRACT

A device for manufacturing a layered material including an elastic thread sandwiched between a pair of sheets, including: a pair of nip rolls arranged with their axes parallel to each other for nipping the elastic thread between the pair of sheets being conveyed in a conveyance direction; a needle arranged upstream of the nip roll in the conveyance direction for guiding and arranging the elastic thread between the pair of sheets while dispensing the elastic thread through a through hole, through which the elastic thread passes; a needle body that holds the needle; a reciprocating section, to which the needle body is attached, for reciprocating in a width direction, which intersects with the conveyance direction; and a stabilizer that stabilizes the reciprocation of the reciprocating section, wherein the stabilizer is a non-contact-type guide.

16 Claims, 8 Drawing Sheets

(51) Int. Cl.
*B32B 5/02* (2006.01)
*B32B 5/26* (2006.01)
*B32B 37/00* (2006.01)
*B32B 37/10* (2006.01)
*B32B 38/00* (2006.01)
*B32B 38/18* (2006.01)

(52) U.S. Cl.
CPC .......... *B32B 5/265* (2021.05); *B32B 37/0046* (2013.01); *B32B 37/10* (2013.01); *B32B 38/18* (2013.01); *B32B 2038/008* (2013.01); *B32B 2250/02* (2013.01); *B32B 2250/20* (2013.01); *B32B 2305/18* (2013.01); *B32B 2307/51* (2013.01); *B32B 2437/00* (2013.01); *B32B 2555/02* (2013.01)

(58) Field of Classification Search
CPC .......... B32B 2038/008; B32B 2250/02; B32B 2250/20; B32B 2305/18; B32B 2307/51; B32B 2437/00; B32B 2555/02; B32B 5/266; B32B 5/06; B32B 37/142; A61F 13/15764; A61F 13/15593

See application file for complete search history.

(56) References Cited

U.S. PATENT DOCUMENTS

2009/0205933 A1\* 8/2009 Sugahara ............ F16H 19/0622
198/618
2016/0242967 A1 8/2016 Wada

FOREIGN PATENT DOCUMENTS

| JP | 2006-230833 A | 9/2006 |
| JP | 2008-51134 A | 3/2008 |
| JP | 2019-138311 A | 8/2019 |
| WO | 2015/053088 A1 | 4/2015 |

\* cited by examiner

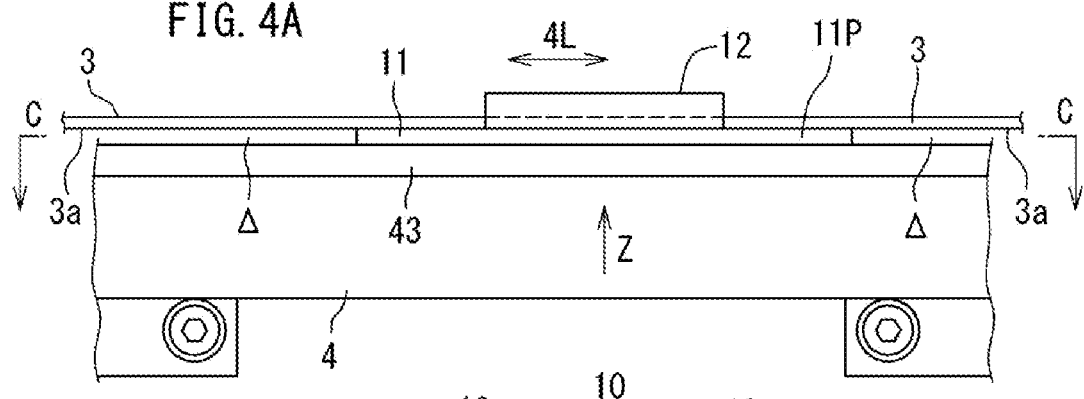
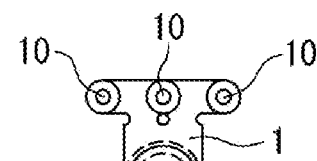
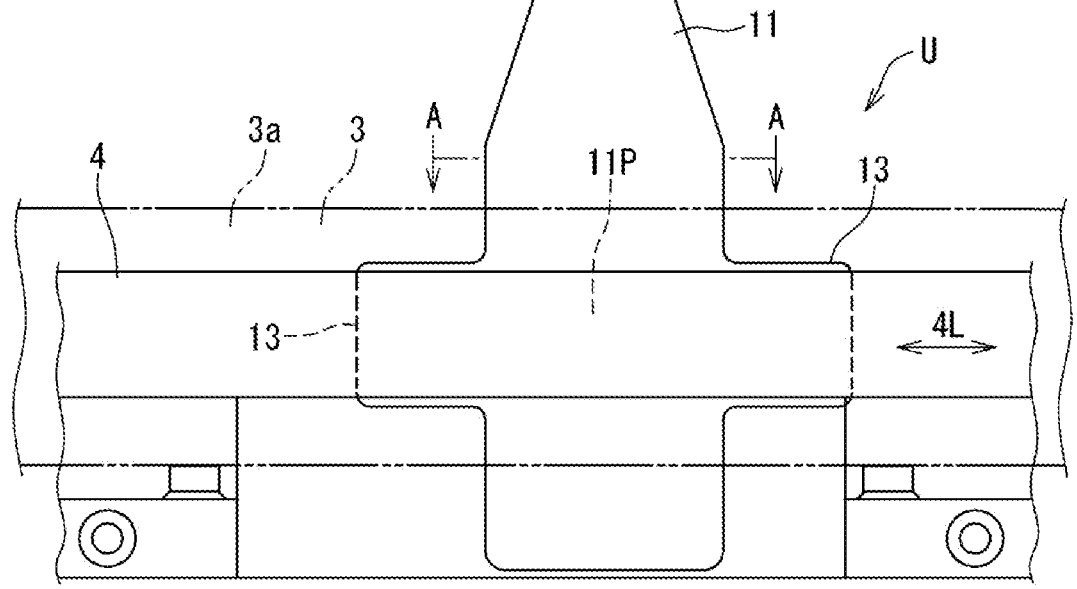
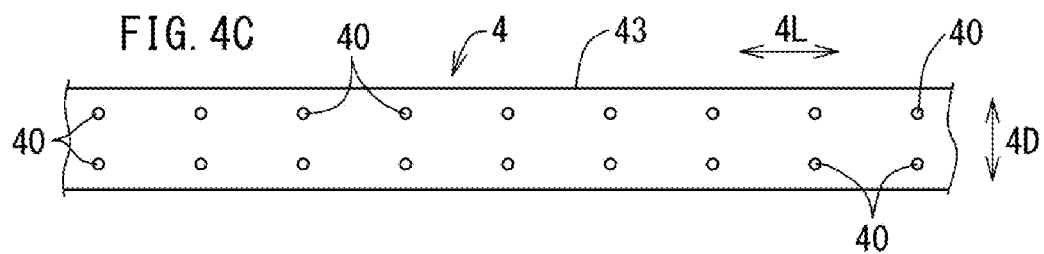

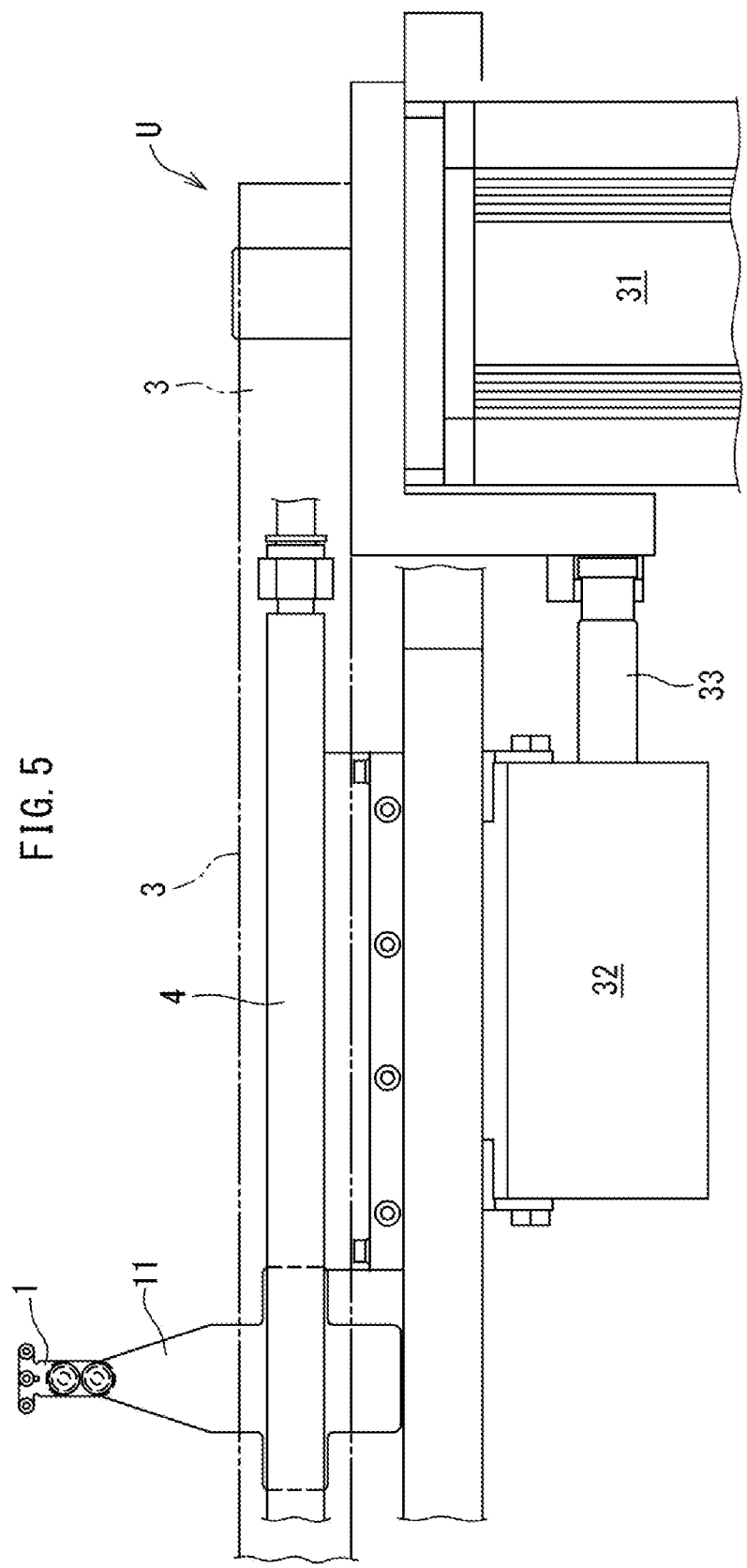

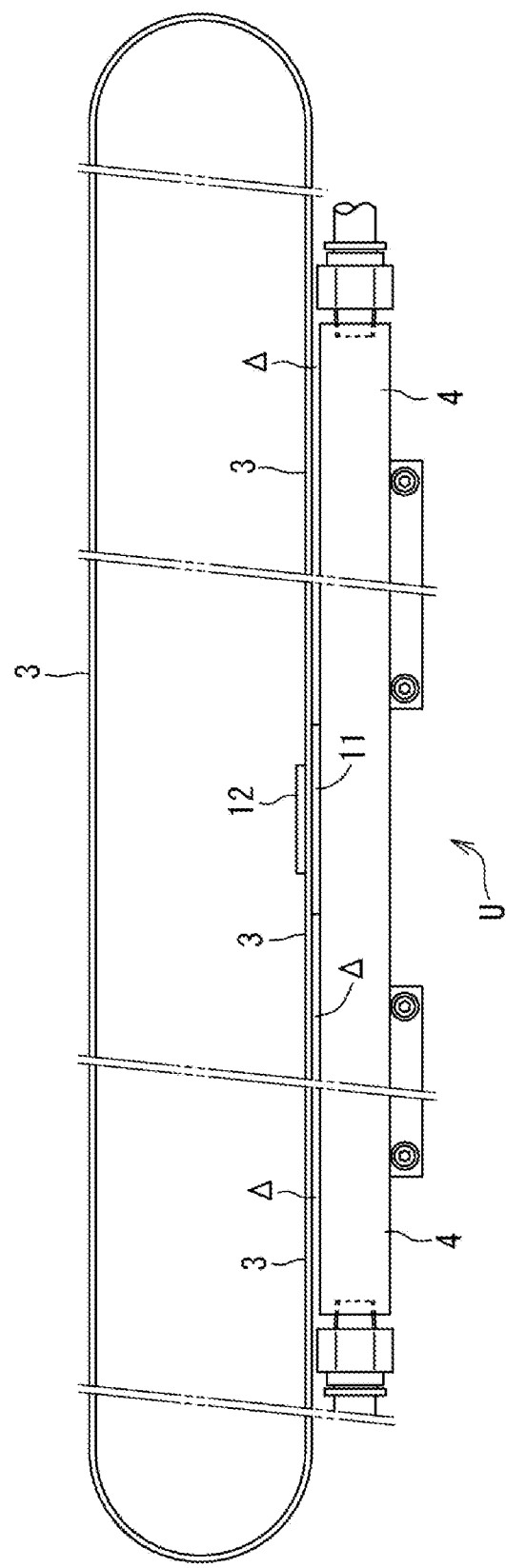

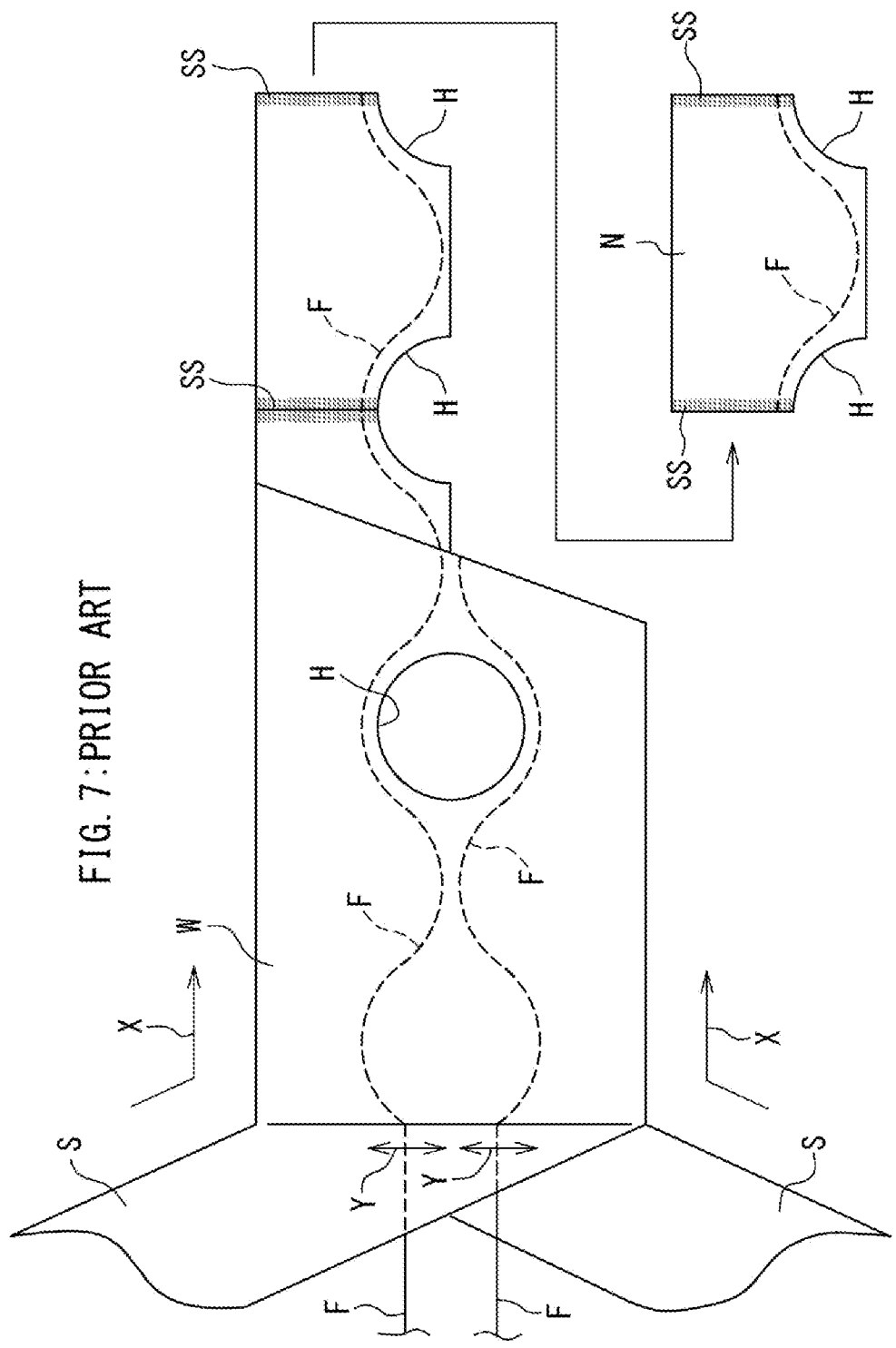
FIG. 7: PRIOR ART

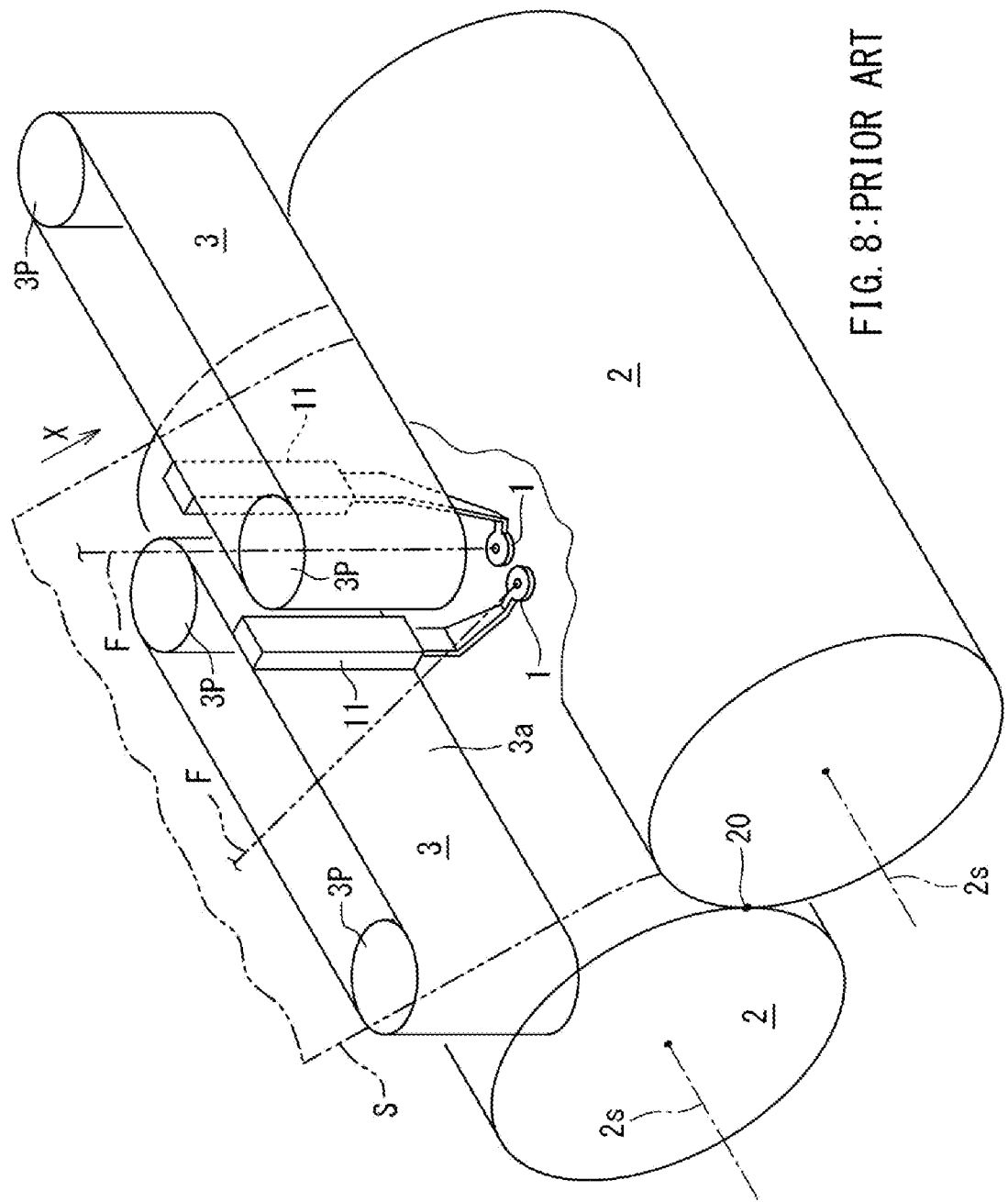
FIG. 8: PRIOR ART

APPARATUS AND METHOD FOR MANUFACTURING LAMINATE

TECHNICAL FIELD

The present invention relates to a device and a method for manufacturing a layered material (a laminate) to be a part of a disposable worn article.

BACKGROUND ART

Elastic threads, so-called rubber threads, are often arranged around the leg holes of disposable pants and diapers.

One conventional example of a device and a method of this type will be described using FIG. 7 and FIG. 8.

FIG. 7 is a conceptual diagram showing a method for manufacturing disposable pants from a layered material W in which elastic threads F are sandwiched between a pair of sheets S, and FIG. 8 is a perspective view of a device for manufacturing the layered material W.

As shown in FIG. 8, the conventional manufacturing device includes a pair of nip rolls 2, a pair of needles 1, a pair of needle bodies 11 and a pair of belts 3. The pair of nip rolls 2 are arranged with their axes 2s parallel to each other.

The pair of needles 1 are arranged upstream of the nip roll 2 in the conveyance direction X of the sheets S for guiding and arranging the elastic threads F between the pair of sheets S of FIG. 7 while dispensing the elastic threads F through through holes 10, through which the elastic threads F pass. The pair of needles 1 of FIG. 8 are held in the needle bodies 11, and the needle bodies 11 are attached to the belts 3. The needle bodies 11 reciprocate with the reciprocating rotation of the belts 3.

The pair of sheets S of FIG. 7 are supplied to the nipping section 20 between the pair of nip rolls 2 of FIG. 8, and a plurality of elastic threads F are supplied meandering in a wave-like form between the sheets. After they are supplied, the layered material W is produced in which the elastic threads F are sandwiched between the pair of sheets S.

Thereafter, after leg holes H are formed in the layered material W, the layered material W is folded in two, sealed at side seals SS, and then cut into individual worn articles N. Thus, a worn article N is produced with the elastic threads F arranged along the leg holes H.

Devices and methods for arranging such elastic threads F are well known in the art (the first patent document).

CITATION LIST

Patent Document

[FIRST PATENT DOCUMENT] WO2015/053088 (FIG. 1 to FIG. 5A)

SUMMARY OF INVENTION

The belts 3 of FIG. 8 are pulled alternately in the direction of rotation by a pair of pulleys 3P as they reciprocate, and thus the tension fluctuates periodically. This periodic tension fluctuation causes the belts 3 to vibrate in a direction orthogonal to surfaces 3a of the belts 3, thereby causing the tips of the needles 1 to vibrate. Therefore, a mechanical guide member such as a linear guide has conventionally been provided to prevent the belts 3 or the needle bodies 11 from vibrating due to the vibration.

However, since the needle bodies 11 and the belts 3 are operated at a high speed, there is a risk that a mechanical guide member such as a linear guide mentioned above may be damaged due to friction. Therefore, there is naturally a limit to increasing the speed of operation.

Thus, an object of the present invention is to provide a device and a method for manufacturing a layered material capable of operating at a higher speed than before.

A manufacturing device of the present invention is a device for manufacturing a layered material W including an elastic thread F sandwiched between a pair of sheets S, including:
  a pair of nip rolls 2 arranged with their axes 2s parallel to each other for nipping the elastic thread F between the pair of sheets S being conveyed in a conveyance direction X;
  a needle 1 arranged upstream of the nip rolls 2 in the conveyance direction X for guiding and arranging the elastic thread F between the pair of sheets S while dispensing the elastic thread F through a through hole 10, through which the elastic thread F passes;
  a needle body 11 that holds the needle 1;
  a reciprocating section, to which the needle body 11 is attached, for reciprocating in a width direction Y, which intersects with the conveyance direction X; and
  a stabilizer that stabilizes the reciprocation of the reciprocating section,
  wherein the stabilizer is a non-contact-type guide 4.

On the other hand, a manufacturing method of the present invention is a method for manufacturing a layered material W including an elastic thread F sandwiched between a pair of sheets 8, the method using a device for manufacturing the layered material W, the device including:
  a pair of nip rolls 2 arranged with their axes 28 parallel to each other for nipping the elastic thread F between the pair of sheets 8 being conveyed in a conveyance direction X;
  a needle 1 arranged upstream of the nip rolls 2 in the conveyance direction X for guiding and arranging the elastic thread F between the pair of sheets S while dispensing the elastic thread F through a through hole 10, through which the elastic thread F passes;
  a needle body 11 that holds the needle 1;
  a reciprocating section, to which the needle body 11 is attached, for reciprocating in a width direction Y, which intersects with the conveyance direction X; and
  a stabilizer that stabilizes the reciprocation of the reciprocating section, the method including:
  a step of continuously supplying the pair of sheets S to a nipping section 20 between the pair of nip rolls 2;
  a step of continuously dispensing and supplying the elastic thread F through the through hole 10 of the needle 1 between the pair of sheets S immediately before the pair of sheets S are supplied to the nipping section 20 between the pair of nip rolls 2;
  a step of reciprocating the reciprocating section in the width direction Y to reciprocate a position of the needle 1 in the width direction Y, thereby arranging the elastic thread F in a wave-like form between the pair of sheets S; and
  a step in which the stabilizer guides the reciprocating section in a non-contact manner by blowing out air or by magnetic force while reciprocating the needle 1.

According to the present invention, the stabilizer stabilizes the reciprocation of the needle 1, and since the stabilizer is of a non-contact type, it causes no friction. Therefore, it is possible to operate at a higher speed than before.

In the present invention, the elastic thread F means a so-called thread rubber, but the material does not need to be rubber and may be any linear continuous elastomer as long as the material has a stretchable property.

In the present invention, the sheet S is continuous in the conveyance direction, and a web (nonwoven fabric) is generally employed as the sheet S.

The term "needle" does not mean a needle-like sharp pointed object, but rather an object which dispenses an elastic thread F from the through hole 10, through which the elastic thread F passes.

BRIEF DESCRIPTION OF THE DRAWINGS

FIG. 4A is a plan view showing a part of a belt and a stabilizer, etc., FIG. 4B is a front view showing a needle and a needle body, etc., and FIG. 4C is a front view showing an outlet surface of the stabilizer.

FIG. 5 is a front view showing a part of a placement unit.

FIG. 6 is a plan view showing a part of a placement unit.

FIG. 7 is a conceptual view showing an example of a method for manufacturing a typical worn article.

FIG. 8 is a perspective view showing a known manufacturing device, partially broken away.

DESCRIPTION OF EMBODIMENTS

Figure 1:
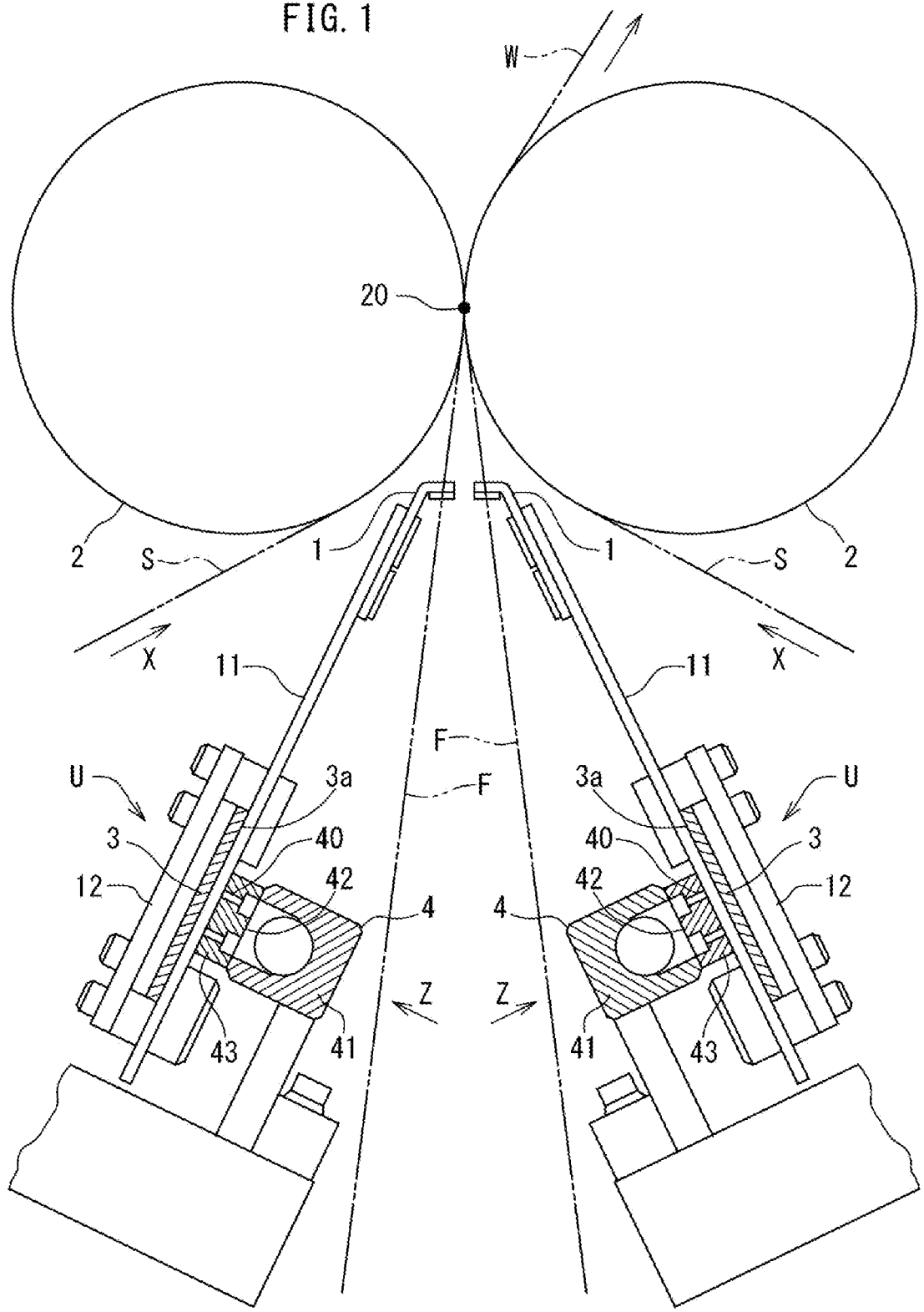
FIG. 1 is a side view showing one embodiment of a device for manufacturing a layered material of the present invention.

The present invention will be understood more clearly from the following description of preferred embodiments taken in conjunction with the accompanying drawings. Note however that the embodiments and the drawings are merely illustrative and should not be taken to define the scope of the present invention. The scope of the present invention shall be defined only by the appended claims. In the accompanying drawings, like reference numerals denote like components throughout the plurality of figures.

An embodiment of the present invention will now be described.

FIG. 1 to FIG. 6 show an embodiment of the present invention.

In FIG. 1, a sheet S is supplied to each of a pair of nip rolls 2, 2, and elastic threads F are supplied between the pair of sheets S, S. The sheets S and the elastic threads F are layered together at the nipping section 20. Note that in FIG. 1, a pair of nip rolls 2 and a pair of placement units U are provided, and the pair of placement units U are provided symmetrically to each other. The pair of nip rolls 2, 2 are in contact with each other in the nipping section 20 with the pair of sheets S and the elastic threads F therebetween.

The needle 1 may be provided with a plurality of through holes 10, through which the elastic threads F pass, as clearly shown in FIG. 4B. As shown in FIG. 1, the needles 1 are held on the needle bodies 11.

The needle body 11 of FIG. 1 is attached to the belt 3. The belt 3 forms a reciprocating section that reciprocates in a width direction Y of FIG. 2, which intersects with the conveyance direction X of the sheet S. The needle 1 and the belt 3 form a part of the placement unit U of the elastic threads F.

Next, the placement unit U will be outlined.

Figure 2:
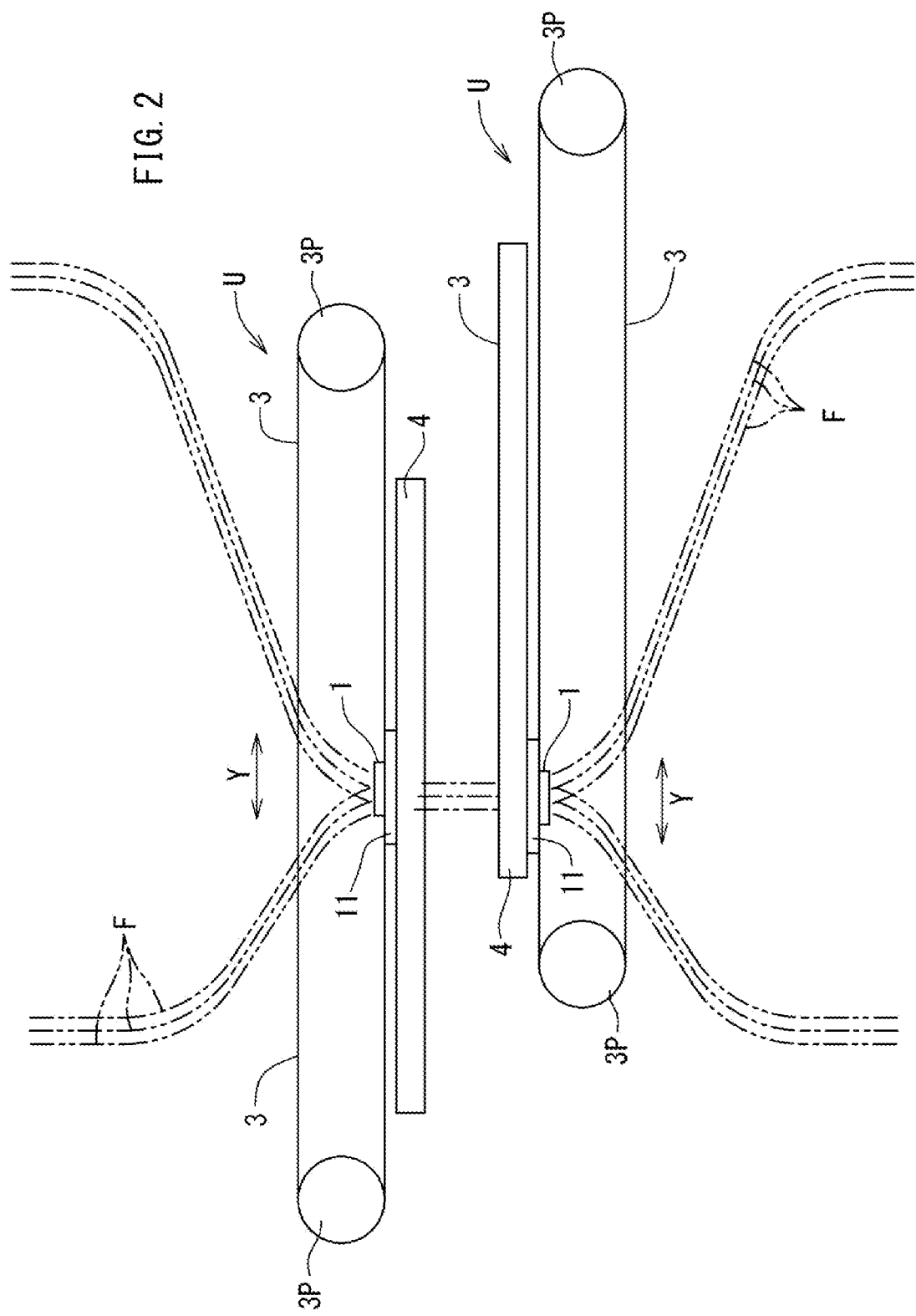
FIG. 2 is a plan (bottom) view of a pair of placement units U.

As shown in FIG. 6, each belt 3 is endless and wound around a pair of pulleys 3P of FIG. 2.

The belt 3 indicated by a two-dot-chain line of FIG. 5 is driven by a motor 31 to reciprocally rotate via the pulleys 8P (FIG. 2). The belt 3 is constantly tensioned by a cylinder 32 via a rod 33, the motor 31 and the pulleys 3P (FIG. 2). The cylinder 32 and the rod 33 prevent the belt 3 from slacking, and form a pressing mechanism that applies tension to the belt 3 so that the needle body 11 is close to a guide 4.

As shown in FIG. 1, the belt 3 is sandwiched between the plate-shaped needle body 11 and a mounting plate 12, and the needle body 11 is attached to the surface 3a of the belt 3. The guide 4 is arranged in the vicinity of the needle body 11 and the belt 3. As shown in FIG. 4A, the guide 4 extends along the surface 3a of the belt 3 relative to the straight portion of the belt 3.

Figure 3:
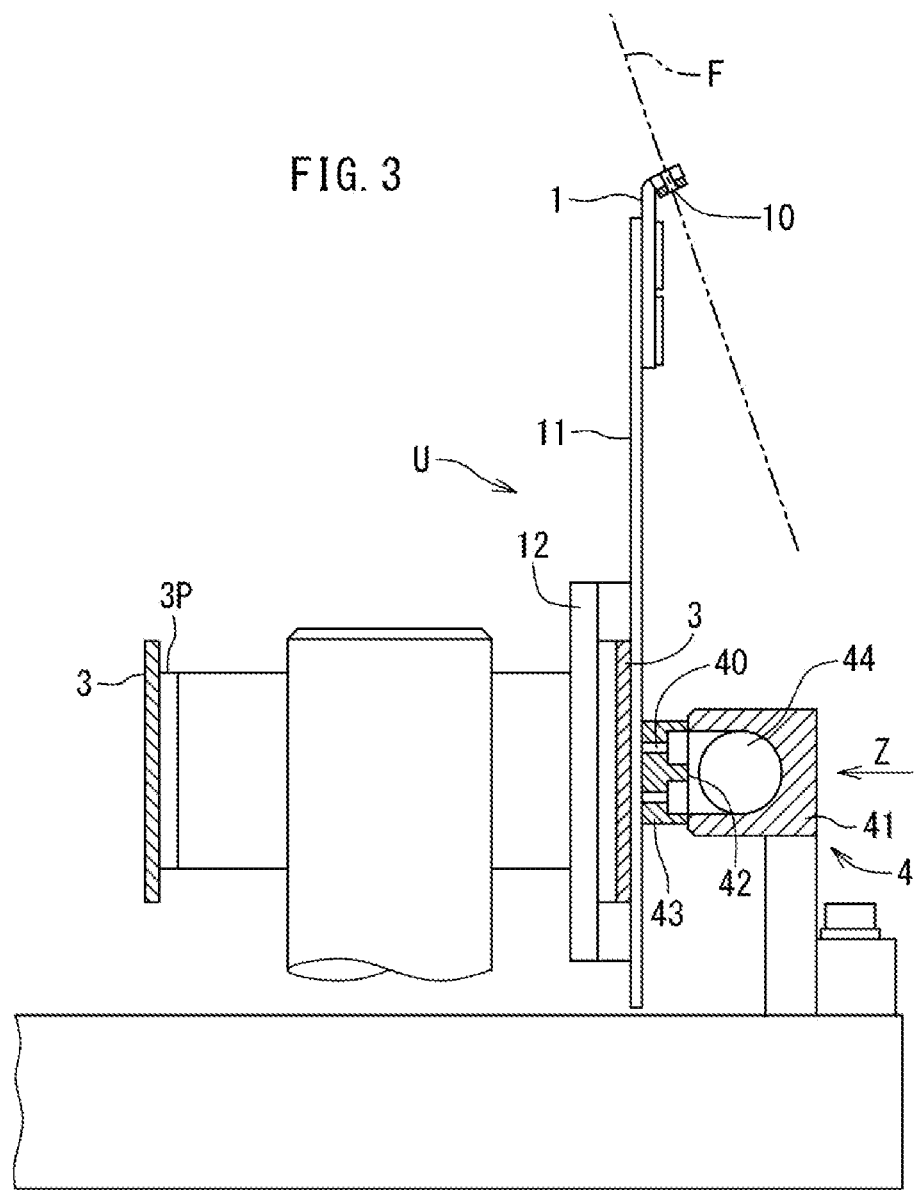
FIG. 3 is a partially-cross-sectional side view of a placement unit.

The guide 4 of FIG. 3 includes an air tank 41 with an air passageway 44 formed therein, the air tank 41 being long along the belt 3, and an air plate 43, which covers an opening 42 formed on one side of the air tank 41 and includes a large number of outlet holes 40. The outlet holes 40 of FIG. 4C are provided intermittently in the longitudinal direction 4L of the guide 4 for blowing out air. That is, the guide 4 of FIG. 4A is configured to push the belt 3, to which the needle body 11 is attached, in the direction Z orthogonal to the surface 3a of the belt 3 by blowing out air.

As shown in FIG. 4B, in this example, the needle body 11 includes a pair of wings 13, 18 projecting in a direction along the guide 4. As clearly shown in FIG. 4A a gap Δ is provided between the belt 3 and the guide 4 by the thickness of the needle body 11. On the other hand, a minute gap is created between the needle body 11 and the guide 4 through which the air flowing out of the outlet holes 40 passes. This gap is so narrow that it cannot be represented in the figure, and forms an air layer. In other words, the needle body 11 of FIG. 4A includes a flat plate portion 11P that is surface-joined to the surface 3a of the belt 3, and an air layer is formed between the flat plate portion 11P and the guide 4 by the air blowing out of the outlet holes 40.

As shown in FIG. 4C, the large number of outlet holes 40 may be arranged in multiple rows (e.g., two rows) spaced apart from each other in the width direction 4D of the belt 3. In this case, the air from the upper row of outlet holes 40 escapes upward and the air from the lower row of outlet holes 40 escapes downward, thereby increasing the probability with which the minute gap between the flat plate portion 11P of the needle body 11 and the guide 4 of FIG. 4A is maintained.

Next, the method for manufacturing the layered material W of FIG. 1 will be described.

As shown in FIG. 1, a pair of sheets S are continuously supplied to the nipping section 20 between the pair of nip rolls 2, and elastic threads F are continuously supplied from the through holes 10 of the needle 1 between the pair of sheets S. In this process, each needle 1, together with the needle body 11, reciprocates in a width direction Y by the drive of the belt 3 of FIG. 2, and the elastic threads F are arranged in a wave-like form, as shown in this figure.

While the needle 1 is reciprocating, air constantly blows out of the outlet holes 40 of the guide 4 of FIG. 3. On the other hand, the belt 3 is under tension as described above, and the air blowing out of the outlet holes 40 pushes the needle body 11 and the belt 3 of FIG. 4A in one direction in the direction Z orthogonal to the surface 3a of the belt 3. Thus, the belt 3 and the needle 1 move in the width direction Y without swinging in the rectangular direction Z.

On the other hand, since the needle body 11 and the belt 3 are not in contact with the guide 4, it is possible to prevent the wear of these parts. Therefore, the belt 3 can operate at a high speed, which improves the productivity of the layered material W.

Otherwise, the structures and the method are similar to the conventional example shown in FIG. 7 and FIG. 8 discussed above, and the detailed description thereof is omitted. The placement unit U of FIG. 1 is described in WO2015/053088 and JP2003-38565A, descriptions of which are all herein incorporated by reference.

The invention conceived from the embodiments described above comprises the following preferred embodiments.

With a preferred manufacturing device, the guide 4 may be a magnetic guide instead of being an air guide. In the case of a magnetic guide, it may be a magnetic guide that makes use of magnetic repulsion.

In the case of these guides, an air layer is formed between the guide 4 and the needle body 11.

That is, there is no limitation on the guide as long as the guide forms an air layer between the guide and the needle body to prevent them from contacting each other.

With a preferred manufacturing device, the reciprocating section is the belt 3;
the needle body 11 is attached to the surface 3a of the belt 3; and
the guide 4 extends along the surface 3a of the belt 3 and is configured to push the belt 3, to which the needle body 11 is attached, in the direction Z orthogonal to the surface 3a of the belt 3 by blowing out air or by magnetic force.

In this case, since the belt 3 is pushed in one direction in the direction Z orthogonal to the conveyance direction X of the belt 3, the belt 3 is unlikely to slack.

With a preferred manufacturing device, the guide 4 has a plurality of outlet holes 40 through which the air is blown out, the outlet holes 40 being arranged intermittently in the longitudinal direction 4L of the guide 4.

In this case, since a plurality of air outlet holes 40 are provided in the longitudinal direction 4L, the force pushing the belt 3 by the blowing of the air is stabilized in the longitudinal direction 4L.

More preferably, a plurality of rows of outlet holes 40 of the guide 4 are provided spaced apart from each other in the width (vertical) direction 4D, which is orthogonal to the longitudinal direction 4L of the guide.

In this case, the air blown out through the plurality of rows of outlet holes 40 spreads out in the width direction 4D and forms a stable air layer.

More preferably, the needle body 11 includes the flat plate portion 11P that is surface-joined to the surface 3A of the belt 3, the flat plate portion 11P facing the guide 4, and an air layer of the air blown out through the outlet holes 40 is formed between the flat plate portion 11P and the guide 4.

In this case, the air layer formed between the guide 4 and the flat plate portion 11P keeps constant the minute gap between the flat plate portion 11P and the guide 4, thereby increasing the probability of realizing the anti-wear effect.

Preferably, the guide 4 includes the air tank 41, which is long along the belt 3, and the air plate 43, which covers the opening 42 formed in the side surface of the air tank 41, the side surface faces the surface of the belt 3, and the outlet holes 40 are formed in the air plate 43.

In this case, the cost of the guide 4 that is long along the belt 3 is reduced.

Preferably, a pressing mechanism is provided for applying tension to the belt 3 so that the flat plate portion 11P is close to the guide 4.

In this case, the tension on the belt 3 keeps the flat plate portion 11P close to the guide 4, and maintains a thin air layer between the guide 4 and the flat plate portion 11P.

Note that it is more preferred that the flat plate portion 11P is in contact with the guide 4 in a non-operating state when air is not blowing out.

With a preferred manufacturing method of the present invention, the stabilizer is the guide 4 extending along the surface 3a of the belt 3 (the reciprocating section); and
in the stabilizing step, the guide 4 presses the belt 3, to which the needle body 11 is attached, in the direction Z orthogonal to the surface 3a of the belt 3 by blowing out air or by magnetic force, thereby suppressing swinging of the belt 3 in the orthogonal direction Z.

This prevents deterioration of the guide due to wear and allows for high speed operation.

Any feature illustrated and/or depicted in conjunction with one embodiment or preferred embodiments may be used in the same or similar form in one or more of the other embodiments, and/or may be used in combination with, or in place of, the other embodiments.

While preferred embodiments have been described above with reference to the drawings, obvious variations and modifications will readily occur to those skilled in the art upon reading the present specification.

For example, only one set of placement units may be provided. The guide may be a magnetic guide using magnetic repulsion instead of air blowing pressure.

Thus, such variations and modifications shall fall within the scope of the present invention as defined by the appended claims.

INDUSTRIAL APPLICABILITY

The present invention can be used as a device and a method for manufacturing a layered material such as a disposable worn article.

REFERENCE SIGNS LIST

1: Needle, 10: Through hole, 11: Needle body, 11P: Flat plate portion
12: Mounting plate, 13: Wing
2: Nip roll, 20: Nipping section, 2s: Axis
3: Belt (reciprocating section), 3a: Surface, 3P: Pulley
31: Motor, 32: Cylinder (pressing mechanism), 33: Rod
4: Guide, 40: Outlet hole, 41: Air tank, 42: Opening, 43: Air plate, 44: Passageway
44: Passageway, 4D: Width direction, 4L: Longitudinal direction
F: Elastic thread
S: Sheet, H: Leg hole, N: Worn article, W: Layered material
X: Conveyance direction, Y: Width direction, Z: Orthogonal direction
U: Placement unit
Δ: Gap

The invention claimed is:

1. A device for manufacturing a layered material including an elastic thread sandwiched between a pair of sheets, comprising:
a pair of nip rolls arranged with their axes parallel to each other for nipping the elastic thread between the pair of sheets being conveyed in a conveyance direction;

a needle arranged upstream of the nip rolls in the conveyance direction for guiding and arranging the elastic thread between the pair of sheets while dispensing the elastic thread through a through hole, through which the elastic thread passes;

a needle body that holds the needle;

a reciprocating section, to which the needle body is attached, for reciprocating in a width direction, which intersects with the conveyance direction; and a stabilizer that stabilizes the reciprocation of the reciprocating section, wherein the stabilizer is a non-contact-type guide, the reciprocating section is a belt, the needle body is attached to a surface of the belt, and the guide extends along the surface of the belt and is configured to push the belt, to which the needle body is attached, in a direction orthogonal to the surface of the belt by blowing out air or by magnetic force.

2. The device for manufacturing a layered material according to claim 1, wherein the guide is an air guide or a magnetic guide.

3. The device for manufacturing a layered material according to claim 1, wherein the guide has a plurality of outlet holes through which the air is blown, the outlet holes being provided intermittently in a longitudinal direction of the guide.

4. The device for manufacturing a layered material according to claim 3, wherein a plurality of rows of the outlet holes of the guide are provided spaced apart from each other in a width direction, which is orthogonal to the longitudinal direction of the guide.

5. The device for manufacturing a layered material according to claim 3, wherein the needle body includes a flat plate portion that is surface-joined to the surface of the belt, the flat plate portion facing the guide, and an air layer of the air blown out through the outlet holes is formed between the flat plate portion and the guide.

6. The device for manufacturing a layered material according to claim 5, wherein a pressing mechanism is provided for applying tension to the belt so that the flat plate portion is close to the guide.

7. The device for manufacturing a layered material according to claim 3, wherein the guide includes an air tank, which is long along the belt, and an air plate, which covers an opening formed in a side surface of the air tank, the side surface facing the surface of the belt, the outlet holes being formed in the air plate.

8. A method for manufacturing a layered material including an elastic thread sandwiched between a pair of sheets, the method using a device for manufacturing the layered material, the device comprising:

a pair of nip rolls arranged with their axes parallel to each other for nipping the elastic thread between the pair of sheets being conveyed in a conveyance direction;

a needle arranged upstream of the nip rolls in the conveyance direction for guiding and arranging the elastic thread between the pair of sheets while dispensing the elastic thread through a through hole, through which the elastic thread passes;

a needle body that holds the needle;

a reciprocating section, to which the needle body is attached, for reciprocating in a width direction, which intersects with the conveyance direction; and a stabilizer that stabilizes the reciprocation of the reciprocating section, the method comprising:

a step of continuously supplying the pair of sheets to a nipping section between the pair of nip rolls;

a step of continuously dispensing and supplying the elastic thread through the through hole of the needle between the pair of sheets immediately before the pair of sheets are supplied to the nipping section between the pair of nip rolls;

a step of reciprocating the reciprocating section in the width direction to reciprocate a position of the needle in the width direction, thereby arranging the elastic thread in a wave-like form between the pair of sheets; and a step in which the stabilizer guides the reciprocating section in a non-contact manner by blowing out air or by magnetic force while reciprocating the needle.

9. The method for manufacturing a layered material according to claim 8, wherein:

the stabilizer is a guide extending along a surface of a belt; and in a stabilizing step, the guide pushes the belt, to which the needle body is attached, in a direction orthogonal to a surface of the belt by blowing out air or by magnetic force, thereby suppressing swinging of the belt in the orthogonal direction.

10. The device for manufacturing a layered material according to claim 4, wherein the guide includes an air tank, which is long along the belt, and an air plate, which covers an opening formed in a side surface of the air tank, the side surface facing the surface of the belt, the outlet holes being formed in the air plate.

11. The device for manufacturing a layered material according to claim 5, wherein the guide includes an air tank, which is long along the belt, and an air plate, which covers an opening formed in a side surface of the air tank, the side surface facing the surface of the belt, the outlet holes being formed in the air plate.

12. The device for manufacturing a layered material according to claim 6, wherein the guide includes an air tank, which is long along the belt, and an air plate, which covers an opening formed in a side surface of the air tank, the side surface facing the surface of the belt, the outlet holes being formed in the air plate.

13. The device for manufacturing a layered material according to claim 4, wherein the needle body includes a flat plate portion that is surface-joined to the surface of the belt, the flat plate portion facing the guide, and an air layer of the air blown out through the outlet holes is formed between the flat plate portion and the guide.

14. The device for manufacturing a layered material according to claim 13, wherein a pressing mechanism is provided for applying tension to the belt so that the flat plate portion is close to the guide.

15. The device for manufacturing a layered material according to claim 13, wherein the guide includes an air tank, which is long along the belt, and an air plate, which covers an opening formed in a side surface of the air tank, the side surface facing the surface of the belt, the outlet holes being formed in the air plate.

16. The device for manufacturing a layered material according to claim 14, wherein the guide includes an air tank, which is long along the belt, and an air plate, which covers an opening formed in a side surface of the air tank, the side surface facing the surface of the belt, the outlet holes being formed in the air plate.

* * * * *